United States Patent
Wheaton et al.

(10) Patent No.: US 11,389,077 B2
(45) Date of Patent: *Jul. 19, 2022

(54) METHOD AND APPARATUS FOR AUTOMATED REGULARIZATION TUNING IN MAGNETIC RESONANCE IMAGING (MRI) USING COMPRESSED SENSING (CS)

(71) Applicant: CANON MEDICAL SYSTEMS CORPORATION, Otawara (JP)

(72) Inventors: Andrew James Wheaton, Vernon Hills, IL (US); Antonios Matakos, Vernon Hills, IL (US); Samir Dev Sharma, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/313,055

(22) Filed: May 6, 2021

(65) Prior Publication Data
US 2021/0315475 A1    Oct. 14, 2021

Related U.S. Application Data

(63) Continuation of application No. 16/370,481, filed on Mar. 29, 2019, now Pat. No. 11,064,901.

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/7203* (2013.01); *G01R 33/4818* (2013.01);
(Continued)

(58) Field of Classification Search
CPC ......... A61B 5/055; A61B 5/7203; A61B 5/00; G06T 11/005; G06T 7/20; G01R 33/5611;
(Continued)

(56) References Cited

U.S. PATENT DOCUMENTS

| 2008/0197842 | A1* | 8/2008 | Lustig .............. G01R 33/5635 324/307 |
| 2012/0177267 | A1 | 7/2012 | Chen et al. |

(Continued)

FOREIGN PATENT DOCUMENTS

CN    103142228 A    6/2013

OTHER PUBLICATIONS

Sathish Ramani, et al. "Regularized Parallel MRI Reconstruction Using an Alternating Direction Method of Multipliers", EECS Department, University of Michigan, Ann Arbor, MI 48109-2122, USA, pp. 385-388.

(Continued)

*Primary Examiner* — Tuan H Nguyen
(74) *Attorney, Agent, or Firm* — Oblon, McClelland, Maier & Neustadt, L.L.P.

(57) ABSTRACT

An apparatus and method are provided to simultaneously provide good image quality and fast image reconstruction from magnetic resonance imaging (MRI) data by selecting an appropriate value for the regularization parameter used in compressed sensing (CS) image reconstruction. In CS reconstruction a high-resolution image can be reconstructed from randomized undersampled data by imposing sparsity in multi-scale transformation (e.g., wavelet) domain. Further, in the transformation domain, a threshold can be determined between signal and noise levels of the transform coefficients. A regularization parameter based on this threshold scales the regularization term, which imposes sparsity, relative to the
(Continued)

data fidelity term in an objective function, thereby balancing the tradeoff between noise and smoothing.

16 Claims, 5 Drawing Sheets

(51) Int. Cl.
*G01R 33/48* (2006.01)
*G06T 11/00* (2006.01)
*G16H 30/40* (2018.01)
*G01R 33/561* (2006.01)
*G01R 33/565* (2006.01)
*G06T 7/20* (2017.01)

(52) U.S. Cl.
CPC ........ *G06T 11/005* (2013.01); *G01R 33/5611* (2013.01); *G01R 33/56509* (2013.01); *G06T 7/20* (2013.01); *G16H 30/40* (2018.01)

(58) Field of Classification Search
CPC .......... G01R 33/56509; G01R 33/4818; G16H 30/40
See application file for complete search history.

(56) References Cited

U.S. PATENT DOCUMENTS

2014/0126796 A1* 5/2014 Chesneau .......... G01R 33/4824
382/131
2015/0257675 A1 9/2015 Bottomley et al.

OTHER PUBLICATIONS

Ilker Bayram and Ivan W. Selesnick. "A Subband Adaptive Iterative Shrinkage/Thresholding Algorithm." IEEE Transactions on Signal Processing, vol. 58, No. 3, Mar. 2010.

* cited by examiner

METHOD AND APPARATUS FOR AUTOMATED REGULARIZATION TUNING IN MAGNETIC RESONANCE IMAGING (MRI) USING COMPRESSED SENSING (CS)

CROSS-REFERENCE TO RELATED APPLICATIONS

This application is a continuation application of and claims the benefit of priority from U.S. application Ser. No. 16/370,481, filed on Mar. 29, 2019; the entire contents of which are incorporated herein.

FIELD

This disclosure relates to magnetic resonance imaging (MRI) using compressed sensing (CS), and, more particularly, to selecting an amount of regularization in the CS reconstruction method to provide good image quality.

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

Medical imaging produces images of the internal members of a patient's body. For example, magnetic resonance imaging (MRI) uses radio waves, magnetic fields, and magnetic-field gradients to produce images of the internal members of a patient's body. Medical-imaging modalities also include, for example, X-ray radiography, ultrasonography, computed tomography (CT), and positron emission tomography (PET). Once the images have been produced, a physician can use the images to diagnose a patient's injuries or diseases.

Also, some medical-imaging devices use compressed sensing (CS). CS reconstructs images using a lower sampling rate than the rate required by the Nyquist-Shannon sampling theorem. CS takes advantage of an image's sparsity within a given domain. Some examples of a domain in which an image may be sparse include the spatial domain (conventional three-dimensional space), time domain (for a time series of images), or wavelet domain (data produced via wavelet transform), CS is able to recover the image using the lower sampling rate using iterative reconstruction methods, which are typically slow and computationally expensive.

The image quality obtained during MRI performed using CS can depend on the degree of regularization. In general, more regularization leads to greater smoothing and less noise, but too much smoothing can lead to blurring and reduced resolution.

In certain implementations of CS, the degree of regularization can be controlled by a regularization parameter $\beta$. For example, CS can be performed by minimizing an objective function that includes a data fidelity term and a regularization term. The regularization term can be scaled by the regularization parameter $\beta$, which multiplies the regularization term, and an optimal value for the regularization parameter $\beta$ will balance the tradeoffs between noise and resolution.

Accordingly, improved methods are desired to select the value of the regularization parameter $\beta$ that is to be applied during CS MRI image reconstruction to optimize image quality.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
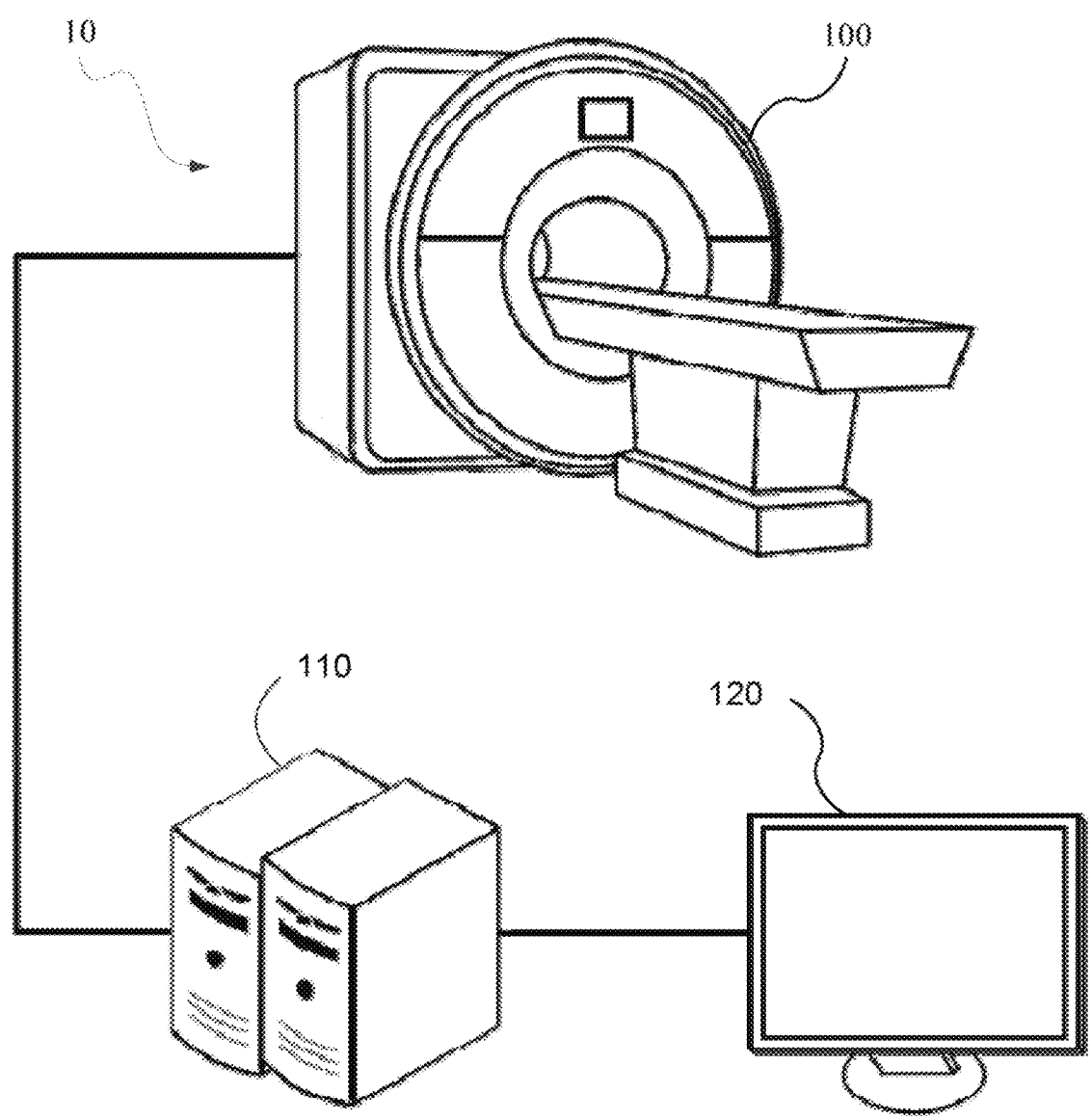
FIG. 1 illustrates a schematic block diagram of an magnetic resonance imaging (MRI) system, according to one implementation.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as 'an embodiment', 'one embodiment', and 'another embodiment' can refer to the same or different embodiments. The embodiments will be described with respect to methods and compositions having certain components. However, the methods and compositions can include more or less components than those shown, and variations in the arrangement and type of the components can be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range—and any other stated or intervening value in that stated range—is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. Any definitions are intended to aid the reader in understanding the present disclosure, but are not intended to vary or otherwise limit the meaning of such terms unless specifically indicated.

As discussed above, improved methods are desired for selecting an optimal value of the regularization parameter $\beta$ that is to be applied during CS magnetic resonance imaging (MRI) image reconstruction.

In certain implementations of CS image reconstruction, the degree of regularization is controlled by a regularization parameter $\beta$ in an objective function. For example, CS reconstruction can be performed by finding the reconstructed image x that minimize an objective function, in which the objective function includes a data fidelity term and a regularization term. Further, the regularization term can express a sparsity condition that favors solutions in which a wavelet (or other) transformation of the reconstructed image x is sparse.

In one non-limiting example, CS reconstruction is performed by solving the optimization problem $$\hat{u} = \operatorname*{argmin}_{u} \|y_R - A_R C W' u\|_2^2 + \beta \|u\|_1,$$

wherein W is a wavelet transformation and W' is an inverse wavelet transformation, $\hat{u}$ and u are the wavelet transformations of the reconstructed image x (i.e., $\hat{u}=W\hat{x}$ and $\hat{x}=W'\hat{u}$), C is a matrix representing the spatial distribution of the receiver coil sensitivities, $y_R$ is the acquired k-space data for all coils with variable density random undersampling of phase encoding (PE) lines, and $A_R$ is a Fourier encoding matrix corresponding to the sampling pattern of the acquisition of $y_R$, such that the Hessian $A'_R A_R$ does not have special structure. Here, the sparsity condition is found in the regularization term $\|u\|_1$, and the sparsity condition is expressed by applying the $\ell_1$ norm (i.e., $\|\cdot\|_1$) to the wavelet transformation u of the reconstructed image x. In the objective function, the expression $\|y_R - A_R C W' u\|_2^2$ is the data fidelity term, which is minimized in order to approximately solve the matrix equation $Ax=y_R$, wherein $A=A_R C$ and $x=W'u$. When the regularization parameter $\beta$ is increased sparser solutions are favored at the expense of lower data fidelity, and, for a smaller regularization parameter $\beta$, improved data fidelity is encouraged at the expense of decreased sparsity. In this model, the regularization parameter $\beta$ balances the relative contributions to the objective functions between data fidelity term and the regularization term.

To select an optimal regularization parameter $\beta$, an iterative method based on the discrepancy principle was suggested in K. F. King et al. "Adaptive regularization in compressed sensing using the discrepancy principle," Proc. Intl. Soc. Mag. Reson. Med. Vol 17, p. 2822 (2009), which is incorporated herein by reference in its entirety. Unfortunately, the discrepancy-principle based approach suffers from being computational intensive. For example, in each of the iterative loops of the discrepancy-principle based approach, CS reconstruction is performed using a given value for the regularization parameter $\beta$, then the regularization parameter $\beta$ is updated based on the reconstructed image and the loop is repeated until the residual of the data fidelity term falls below a desired noise threshold. This can be slow because the CS reconstruction performed in each loop requires significant computations. In contrast, the methods described herein estimate the best regularization parameter $\beta$ before performing CS reconstruction, such that CS reconstruction is only performed once, resulting in significant computational savings.

Referring now to the drawings, wherein like reference numerals designate identical or corresponding parts throughout the several views, FIG. 1 illustrates an example embodiment of a medical-imaging system 10. The medical-imaging system 10 includes at least one scanning device 100; one or more image-generation devices 110, each of which is a specially-configured computing device (e.g., a specially-configured desktop computer, a specially-configured laptop computer, a specially-configured server); and a display device 120.

The scanning device 100 is configured to acquire scan data by scanning a region (e.g., area, volume, slice) of an object (e.g., a patient). The scanning modality may be, for example, magnetic resonance imaging (MRI), computed tomography (CT), positron emission tomography (PET), X-ray radiography, and ultrasonography. The scanning device 100 may acquire a randomly undersampled set of scan data that is appropriate for CS reconstruction or acquire scan data that may be used by a CS process. Accordingly, CS data includes scan data that may be used by a CS process or that is appropriate for CS reconstruction.

The one or more image-generation devices 110 obtain scan data from the scanning device 100 and generate an image of the region of the object based on the scan data. To generate the image, for example when the scan data is CS data, the one or more image-generation devices 100 may perform a reconstruction process on the scan data. Examples of reconstruction processes include GRAPPA, SENSE, ARC, SPIRiT, LORAKS, ISTA, and FISTA. For CS data, the reconstruction process can be a non-linear process that enforces both the sparsity of the image representation within a given domain (e.g., spatial, time, wavelet) and the consistency of the reconstruction with the acquired scan data.

After the one or more image-generation devices 110 generate the image, the one or more image-generation devices 110 send the image to the display device 120, which displays the image.

Also, the one or more image-generation devices 110 may generate two images from the same scan data. The one or more image-generation devices 110 may use different reconstruction processes to generate the two images from the same scan data, and one image may have a lower resolution than the other image. Additionally, the one or more image-generation devices 110 may generate an image.

Figure 2:
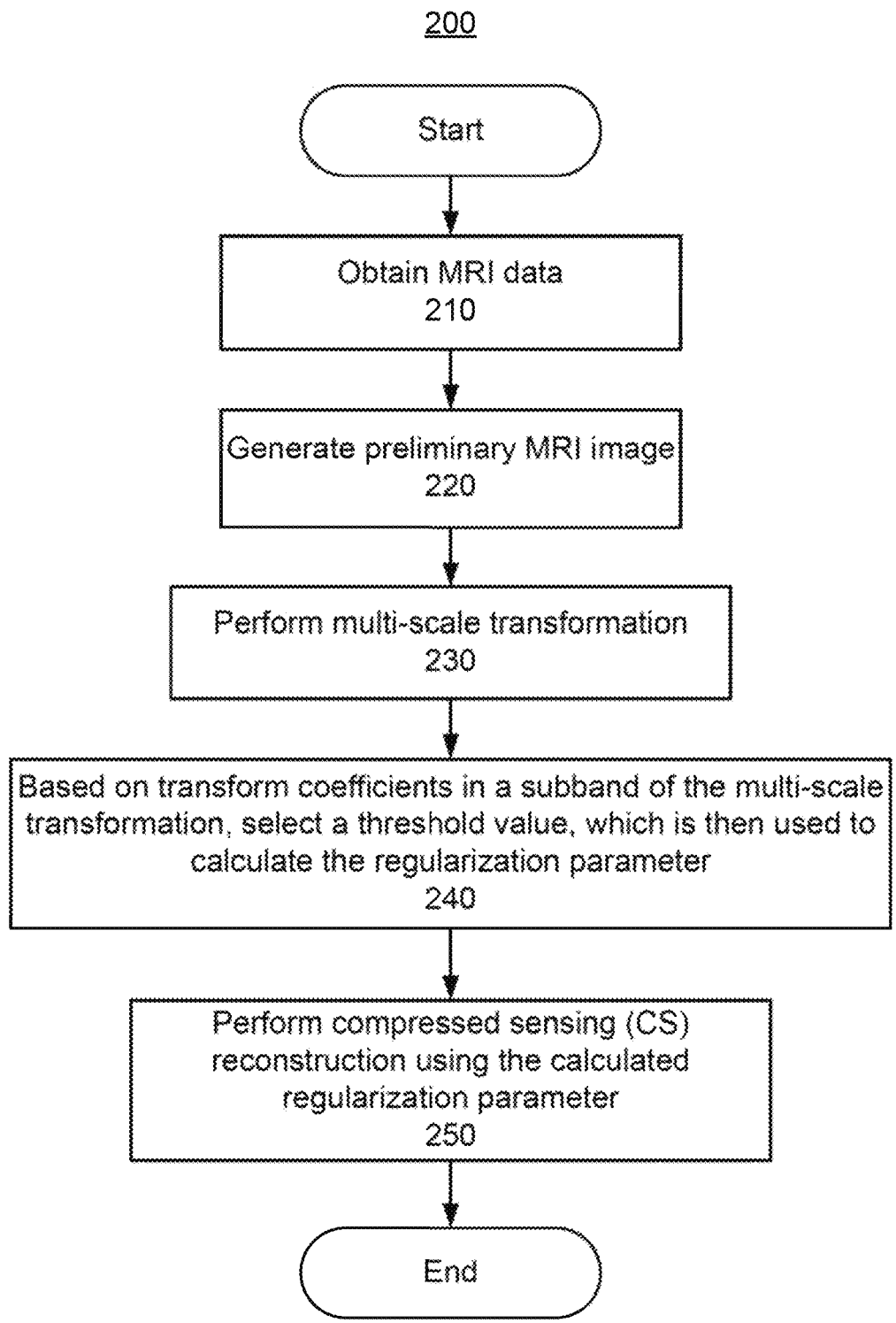
FIG. 2 illustrates a flow diagram of a method for determining a regularization parameter and applying it to compressed sensing (CS) image reconstruction, according to one implementation.

FIG. 2 illustrates a non-limiting example of a flow diagram for using CS to reconstruct an MRI image. In addition to this non-limiting example, other flow diagrams may be used. For example, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks.

Furthermore, although this flow diagram is described as being performed by an image-generation device, some embodiments of the flow diagram can be performed by two or more image-generation devices or by one or more other specially-configured computing devices.

In step 210 of method 200, the image-generation device obtains scan data, which are defined in an acquisition space. For example, if the scan modality is MRI, then the acquisition space may be k-space, and the k-space data may be acquired using collection methods such as Cartesian sampling, spiral sampling, and radial sampling. Here, method 200 is illustrated for a case of MRI data sampled for CS, as would be understood by a person of ordinary skill in the art.

In step 210 of method 200, a preliminary image is generated. For example, the MRI data from step 210 can be acquired in k spaces through randomized undersampling. Then, the preliminary image can be generated by zero filing the under-sampled MRI data and back-projecting to the image domain to generate a preliminary image. That is, the sampled data $y_R$ can be zero-filled to generate zero-filled data $\tilde{y}_R$ in k-space, then the zero-filled data $\tilde{y}_R$ can be back-projected $x_0 = A'\tilde{y}_R$ to generate the preliminary image $x_0$, wherein A' is the back-projection operator, which is the adjoint to the forward-projection operator A.

This preliminary image $x_0$ can also be used to provide a warm start for iterative reconstruction using a CS method. CS reconstruction can be performed as an iterative method that searches for the reconstructed image x that minimizes an objective function. This search starts with an initial guess for the reconstructed image x, and a warm start (i.e., the preliminary image) can shorten the search by providing an initial guess for the search that is at least an informed approximation of the final reconstructed image x. Other methods, besides back-projecting the zero-filled MRI data, can also be used to generate a preliminary image $x_0$.

In certain implementations, the preliminary image $x_0$ that is used for determining the regularization parameter may or may not be the same as the initial guess for iterative reconstruction using the CS reconstruction method.

In step 230 of method 200, a multi-scale transformation is performed on the preliminary image $x_0$. To illustrate method 200, the wavelet transformation is used as one example of a multi-scale transformation. However, other multi-scale transformations can be used without departing from the spirit of the invention. Examples, of other multi-scale transformations that can be used include: Haar transformations, Gabor transformations, curvelet transformations, Gaussian pyramid transformations, Laplacian pyramid transformations, steerable pyramid transformations, blocked discrete cosine transformations, and blocked discrete Fourier transformations.

Continuing with the non-limiting example that step 230 is performed using a wavelet transformation, the preliminary image $x_0$ is transformed into wavelet coefficients corresponding to different subbands (e.g., a low-low subband, a low-high subband, a high-low subband, and a high-high subband). In this example, the high-high subband is a fine-scale subband, and the low-low subband is a coarse-scale subband. The low-high subband and the high-low subband would each represent features that are large/coarse in one spatial dimension and small/fine in another spatial dimension.

In step 240 of method 200, a thresholding method is applied to the wavelet coefficients of one of the subbands (e.g., the finest-scale subband) to determine a threshold value. The threshold value is then used in turn to calculate regularization parameter to be used in CS reconstruction.

In one example of an implementation of step 240, a threshold value is selected based on the transform coefficients of the finest scale subband of the multi-scale transformation. This threshold value can be selected, e.g., using a histogram of the wavelet coefficients in the finest-scale subband of the wavelet transformation, and selecting the coefficient value of the Nth percentile of the histogram. In certain implementations, the Nth percentile of the histogram can be the 99th percentile of the histogram. The Nth percentile of the histogram can be such that the number of coefficients in the subband having values below the threshold is one order of magnitude greater than the number of coefficients in the subband having values greater than the threshold. In other implementations, the Nth percentile of the histogram can be such that the number of coefficients in the subband having values below the threshold is two orders of magnitude greater than the number of coefficients in the subband having values greater than the threshold.

For example, 10-20% of the coefficients in the subband can have values greater than the threshold. In another implementation, 5-10% of the coefficients in the subband can have values greater than the threshold. In a third implementation, 2.5-5% of the coefficients in the subband can have values greater than the threshold. In a fourth implementation, 1-2.5% of the coefficients in the subband can have values greater than the threshold.

In certain implementations, the regularization parameter is equal to the threshold value. In other implementations, the regularization parameter is calculated using a function which includes the threshold value as one of its inputs.

Although, the determination of the threshold value is illustrated using the example of a histogram based method, other methods of determining the threshold value can be used without departing from the spirit of the invention. For example, the threshold value can be determined using an Otsu's method.

Otsu's method is used to automatically perform clustering-based image thresholding. In Otsu's method, the algorithm assumes that the image contains two classes of pixels following bi-modal histogram (foreground pixels and background pixels). The optimum threshold separating the two classes is then calculated so that their combined spread (intra-class variance) is minimal. That is, the optimum threshold separating the two classes is then calculated so that their inter-class variance is maximal or equivalently (i.e., the sum of pairwise squared distances is constant). Otsu's method can be better understood by noting that it is roughly a one-dimensional, discrete analog of Fisher's Discriminant Analysis, and that Otsu's method is also directly related to the Jenks optimization method.

Further, in certain implementations, the threshold value can be determined using any one of a clustering-based thresholding method, a k-means clustering method, and/or a mixture-model based method.

In step 250 of method 200, CS reconstruction is performed on the MRI data using an objective function in which the relative contributions between the data fidelity term and the regularization term is based on the threshold determined in step 240. In general, the image reconstruction method can be any regularizer method (i.e., an image reconstruction method that minimizes an objective function that includes a regularizer/regularization term), and is not limited to CS methods.

For example, in the case that the image x=W'u is reconstructed by minimizing the above objective function $$\|y_R - A_R CW'u\|_2^2 + \beta\|u\|_1,$$

the regularization parameter $\beta$ can be set equal to the threshold value itself, which is the value of Nth percentile of a histogram of the finest-scale subband of a wavelet transformation. More generally, the regularization parameter β can be a function of the threshold value.

The threshold value estimates a division between noise and signal values in the wavelet coefficients. The assumption of CS is that, in the transform/wavelet domain, the transform/wavelet coefficients expressing signal will be sparse, whereas most wavelet coefficients represent noise predominantly. This sparsity assumption can be even stronger in the finer-scale subbands than in the coarser-scale subbands, especially when most of the signal is expressed at lower spatial frequencies. Thus, the threshold value determined in step 240 can estimate a cutoff demarking the boundary between coefficient values that represent signal and those that represent noise. This estimated threshold provides an appropriate scaling factor to relate the regularization term to the data fidelity term of the objective function. Further, by selecting the threshold based on the wavelet transformation of the MRI data itself, the determination of the regularization parameter is robust against variations in the patient's size, factors affecting the signal and noise levels, acceleration factors, coil choice, the MRI scanner setup, geometry, and orientation.

The choice of N in the Nth percentile of a histogram can be selected based on empirical factors and observations in order to obtain preferred image characteristics and quality. Advantageously, the empirical tuning only needs to happen once (e.g., in the factory)—not on a per protocol basis.

In addition to the non-limiting example of method 200 discussed above, variations of the method can be implemented without departing from the spirit of the invention. In the above-described implementation, a regularization parameter is based on the threshold from the finest-scale subband, and this regularization parameter can be used for all subbands.

In other implementations, the regularization parameter can be based on a threshold that is determined using a different subband than the finest-scale subband, and this regularization parameter can be used for all subbands.

In still other implementations, multiple regularization parameters can be used, and these different regularization parameters can be based on respective thresholds estimated from various subbands of the multi-scale transformation. Then, these different regularization parameters can be used for different regularization terms in the objective function. For example, objective function might include that the regularization term is split into two or more regularization terms. In certain implementations, the objective function can include a fine regularization term and a coarse regularization term, i.e., $$\hat{u} = \underset{u}{\operatorname{argmin}} \|y_R - A_R CW'u\|_2^2 + \beta_H \|u_H\|_1 + \beta_L \|u_L\|_1,$$

wherein $u=\{u_L, u_H\}$ and $u_H$ is one subset of the wavelet subbands (e.g., the fine subbands) and $u_L$ is another subset of the rest of the wavelet subbands (e.g., the coarse subbands). Then the first regularization parameter $\beta_H$ can be based on a subband from the first subset $u_H$ of the wavelet subbands. Further, the second regularization parameter $\beta_L$ can be based on a subband from the second subset $u_L$ of the wavelet subbands.

More generally, the subbands can be partitioned into any number L of subsets, and the objective function can be expressed as $$\hat{u} = \underset{u}{\operatorname{argmin}} \|y_R - A_R CW'u\|_2^2 + \sum_{i=1}^{L} \beta_i \|u_i\|_1,$$

wherein $u=\{u_1, u_2, \ldots, u_L\}$. For example, the number L of subsets can be equal to the number of subbands. Then, for each subband, the threshold and regularization parameter would be based on a thresholding method performed on the transform coefficients of the respective subband.

In still other implementations, threshold values from multiple subbands can be averaged/combined to generate a single regularization parameter.

Alternatively, the noise can be extracted/estimated in k-space, and then back-projected into the image domain before performing the multi-scale transformation to generate respective subbands. In this case, each subband would represent isolated noise, without any signal. The threshold could then be estimated based on the noise alone. For example, the noise can be estimated/measured by performing calibration scan without exciting the nuclear spins.

Figure 3A:
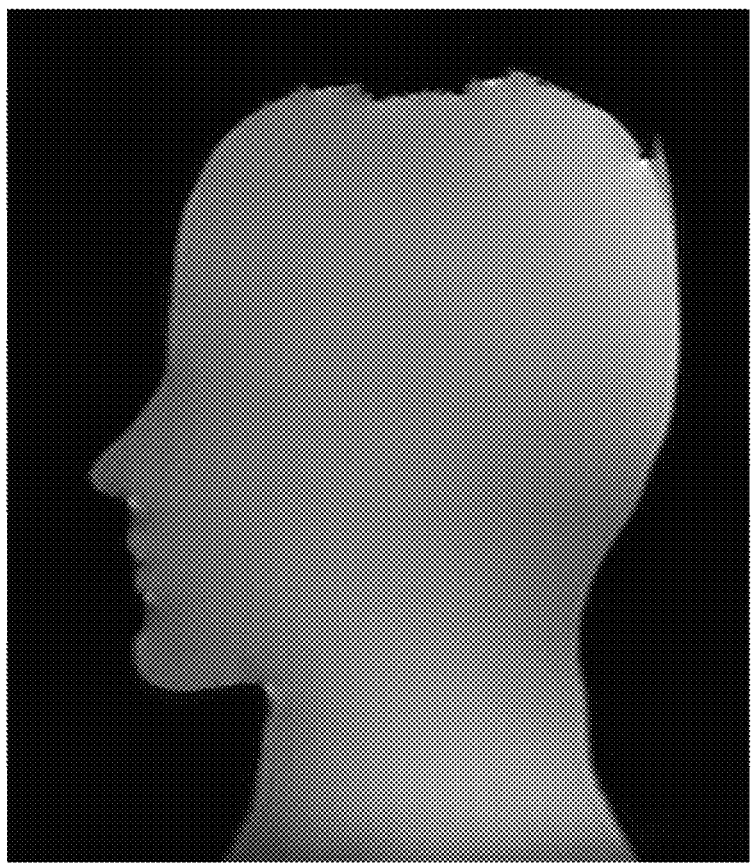
FIG. 3A illustrates a reconstructed image of a head phantom, generated using a regularization parameter selected by a user, according to one implementation.
Figure 3B:
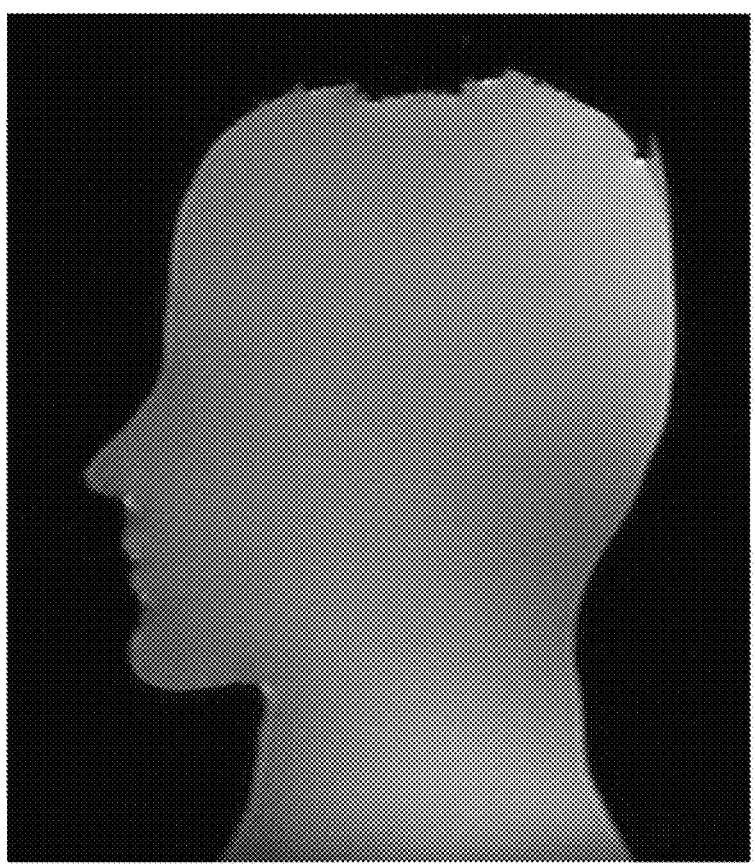
FIG. 3B illustrates a reconstructed image of the head phantom, generated using a regularization parameter selected by an automated method described herein, according to one implementation.

FIGS. 3A and 3B show reconstructed images from MRI data from a head phantom. FIG. 3A shows the reconstructed image when the regularization parameter, which was selected by a user was too high (i.e., 2.0), resulting in the regularization/sparsity condition being overemphasized relative to the data fidelity condition. This overemphasis on sparsity results in the periodic, vertical striation artifact observable in the neck region. FIG. 3B shows the reconstructed image when the regularization parameter is determined using the method described herein. In FIG. 3B, the regularization parameter is set to 0.8 rather than 2.0. By decreasing the regularization parameter to a more optimal value, the striation artifact is mitigated.

Figure 4A:
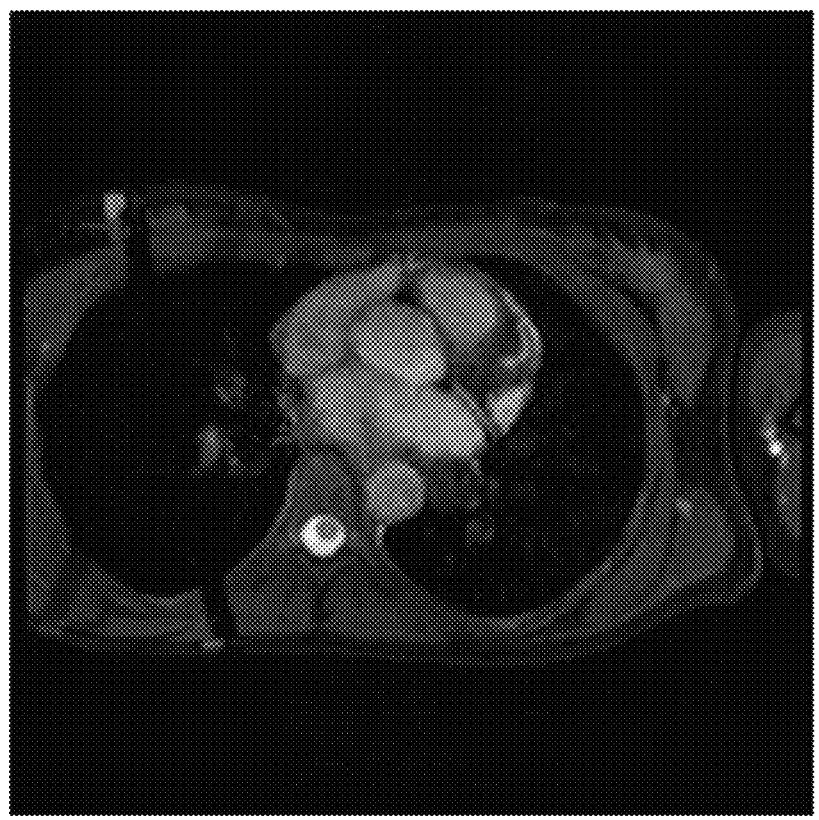
FIG. 4A illustrates a reconstructed image of a chest, generated using a regularization parameter selected by a user, according to one implementation.
Figure 4B:
FIG. 4B illustrates a reconstructed image of the chest, generated using a regularization parameter selected by the automated method described herein, according to one implementation.

FIGS. 4A and 4B show reconstructed images from MRI data of a chest. Here, like in FIG. 3A, FIG. 4A shows an image in which the user selected by a user regularization parameter was too high (i.e., 2.8), resulting in too much smoothing, although there are no obvious artifacts. FIG. 4B shows the reconstructed image when the regularization parameter is determined using the method described herein. In FIG. 4B, the regularization parameter is set to 1.36 rather than 2.8. By decreasing the regularization parameter to a more optimal value, the structure within the soft tissue and the lungs becomes more visible.

In summary, the methods described herein for automatically determining the regularization parameter have several advantages. First, the methods described herein simplify workflow and decrease the opportunities for error by eliminating the requirement for human interaction to select the regularization parameter. Further, the methods described herein provide optimization of the image quality by balancing the trade-offs between noise and smoothing/blurring. Third, the methods described herein are robust to changes in protocols, patient size, accelerations factors, noise/signal levels, etc., thereby providing image quality consistency for all protocols. Fourth, the methods described herein are fast because they can be performed with a preliminary image, and do not require an iterative process in which each loop includes CS image reconstruction. Accordingly, the methods described herein add little additional computation time to existing CS reconstruction methods. This achieves significant computation and time savings relative to discrepancy-principle based methods, which require multiple, sequential CS reconstructions.

Figure 5:
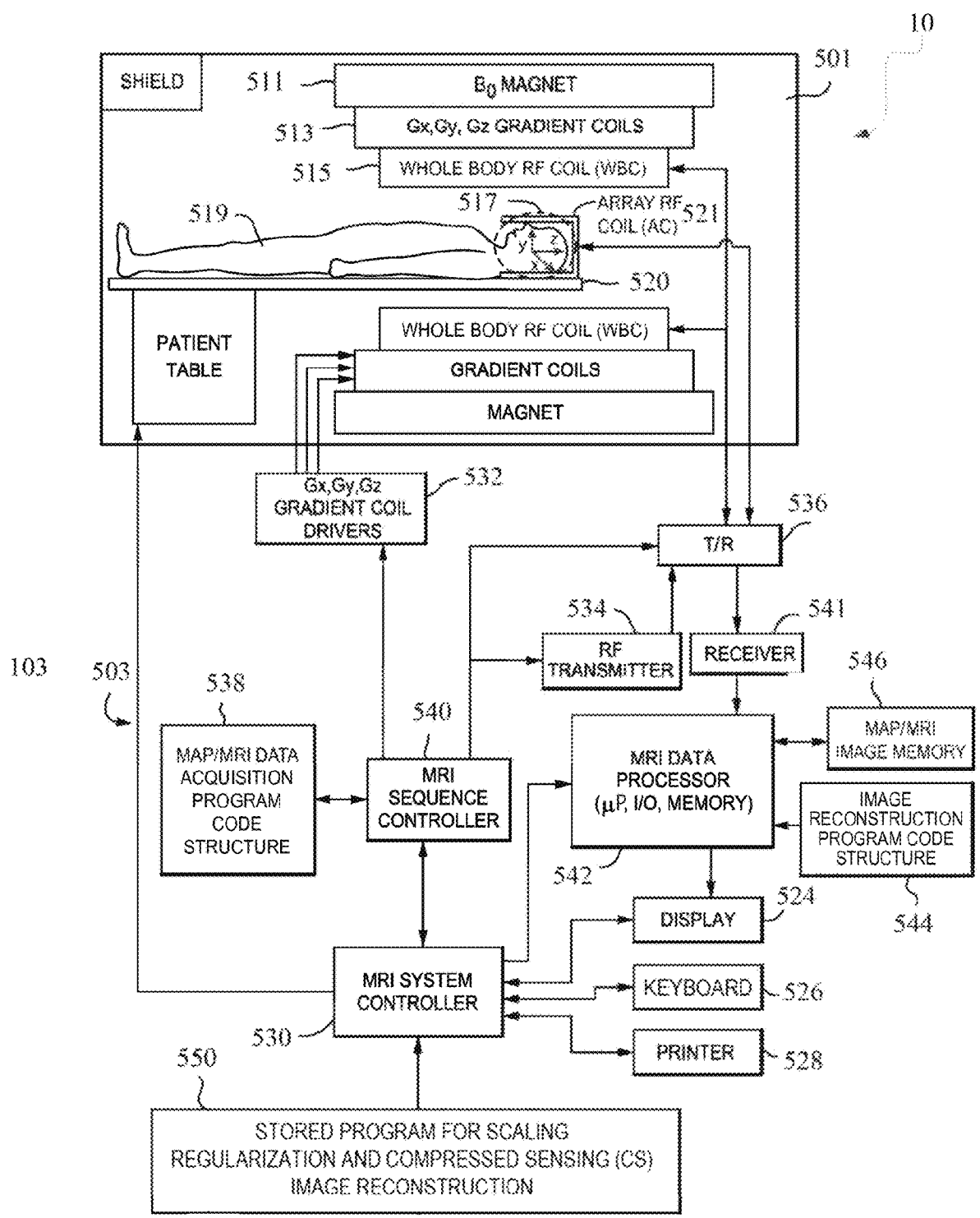
FIG. 5 illustrates a more detailed schematic block diagram of the MRI system.

FIG. 5 shows a non-limiting example of a magnetic resonance imaging (MRI) system 10. The MRI system 10 depicted in FIG. 5 includes a gantry 501 (shown in a schematic cross-section) and various related system components 503 interfaced therewith. At least the gantry 501 is typically located in a shielded room. The MRI system geometry depicted in FIG. 5 includes a substantially coaxial cylindrical arrangement of the static field $B_0$ magnet 511, a Gx, Gy, and Gz gradient coil set 513, and a large whole-body RF coil (WBC) assembly 515. Along a horizontal axis of this cylindrical array of elements is an imaging volume 517 shown as substantially encompassing the head of a patient 519 supported by a patient table 520.

One or more smaller array RF coils 521 can be more closely coupled to the patient's head (referred to herein, for example, as "scanned object" or "object") in imaging volume 517. As those in the art will appreciate, compared to the WBC (whole-body coil), relatively small coils and/or arrays, such as surface coils or the like, are often customized for particular body parts (e.g., arms, shoulders, elbows, wrists, knees, legs, chest, spine, etc.). Such smaller RF coils are referred to herein as array coils (AC) or phased-array coils (PAC). These can include at least one coil configured to transmit RF signals into the imaging volume, and a plurality of receiver coils configured to receive RF signals from an object, such as the patient's head, in the imaging volume.

The MRI system 10 includes a MRI system controller 530 that has input/output ports connected to a display 524, a keyboard 526, and a printer 528. As will be appreciated, the display 524 can be of the touch-screen variety so that it provides control inputs as well. A mouse or other I/O device(s) can also be provided.

The MRI system controller 530 interfaces with a MRI sequence controller 540, which, in turn, controls the Gx, Gy, and Gz gradient coil drivers 532, as well as the RF transmitter 534, and the transmit/receive switch 536 (if the same RF coil is used for both transmission and reception). The MRI sequence controller 540 includes suitable program code structure 538 for implementing MRI imaging (also known as nuclear magnetic resonance, or NMR, imaging) techniques including parallel imaging. MRI sequence controller 540 can be configured for MR imaging with or without parallel imaging. Moreover, the MRI sequence controller 540 can facilitate one or more preparation scan (pre-scan) sequences, and a scan sequence to obtain a main scan magnetic resonance (MR) image (referred to as a diagnostic image). MR data from pre-scans can be used, for example, to determine sensitivity maps for RF coils 515 and/or 521 (sometimes referred to as coil sensitivity maps or spatial sensitivity maps), and to determine unfolding maps for parallel imaging.

The MRI system components 503 include an RF receiver 541 providing input to data processor 542 so as to create processed image data, which is sent to display 524. The MRI data processor 542 is also configured to access previously generated MR data, images, and/or maps, such as, for example, coil sensitivity maps, parallel image unfolding maps, distortion maps and/or system configuration parameters 546, and MRI image reconstruction program code structures 544 and 550.

In one embodiment, the MRI data processor 542 includes processing circuitry. The processing circuitry can include devices such as an application-specific integrated circuit (ASIC), configurable logic devices (e.g., simple programmable logic devices (SPLDs), complex programmable logic devices (CPLDs), and field programmable gate arrays (FPGAs), and other circuit components that are arranged to perform the functions recited in the present disclosure.

The processor 542 executes one or more sequences of one or more instructions contained in the program code structures 544 and 550 (e.g., method 200). Alternatively, the instructions can be read from another computer-readable medium, such as a hard disk or a removable media drive. One or more processors in a multi-processing arrangement can also be employed to execute the sequences of instructions contained in the program code structures 544 and 550 (e.g., method 200). In alternative embodiments, hard-wired circuitry can be used in place of or in combination with software instructions. Thus, the disclosed embodiments are not limited to any specific combination of hardware circuitry and software.

Additionally, the term "computer-readable medium" as used herein refers to any non-transitory medium that participates in providing instructions to the processor 542 for execution. A computer readable medium can take many forms, including, but not limited to, non-volatile media or volatile media. Non-volatile media includes, for example, optical, magnetic disks, and magneto-optical disks, or a removable media drive. Volatile media includes dynamic memory.

Also illustrated in FIG. 5 is a generalized depiction of an MRI system program storage (memory) 550, where stored program code structures are stored in non-transitory computer-readable storage media accessible to the various data processing components of the MRI system 10. As those in the art will appreciate, the program store 550 can be segmented and directly connected, at least in part, to different ones of the system 503 processing computers having most immediate need for such stored program code structures in their normal operation (i.e., rather than being commonly stored and connected directly to the MRI system controller 530).

While certain implementations have been described, these implementations have been presented by way of example only, and are not intended to limit the teachings of this disclosure. Indeed, the novel methods, apparatuses and systems described herein can be embodied in a variety of other forms; furthermore, various omissions, substitutions and changes in the form of the methods, apparatuses and systems described herein can be made without departing from the spirit of this disclosure.

The invention claimed is:

1. An imaging apparatus, comprising:
   processing circuitry configured to
   obtain magnetic resonance imaging (MRI) data, the MRI data being acquired by non-uniformly sampling k-space,
   perform a multi-scale transformation on a preliminary image generated from the MRI data and generating thereby a plurality of subbands, each of the plurality of subbands comprising respective transformation coefficients of the multi-scale transformation,
   determine, based on at least one of the plurality of subbands, a threshold between signal and noise of the transformation coefficients, and
   reconstruct an MRI image from the MRI data using a regularized method in which an objective function is minimized, the objective function including a data fidelity term and a regularization term that is scaled based on the determined threshold between the signal and the noise of the transformation coefficients.

2. The apparatus according to claim 1, wherein the processing circuitry is further configured to determine the threshold using at least one of a clustering-based thresholding method, an Otsu's method, a k-means clustering method, and a mixture-model based method.

3. The apparatus according to claim 1, wherein the processing circuitry is further configured to perform the multi-scale transformation, wherein the multi-scale transformation is one of a wavelet transformation, a curvelet transformation, a Gaussian pyramid, a Laplacian pyramid, a steerable pyramid, a Gabor transformation, a blocked discrete cosine transformation or blocked discrete Fourier transformation, and/or a Haar transformation.

4. The apparatus according to claim 1, wherein the processing circuitry is further configured to reconstruct the MRI image from the MRI data using respective thresholds corresponding to respective subbands of the plurality of subbands, each of the respective thresholds scaling a respective regularization term of the objective function corresponding to a respective subband.

5. The apparatus according to claim 1, wherein the processing circuitry is further configured to reconstruct the MRI image from the MRI data by minimizing the objective function, wherein the regularization term of the objective function imposes sparsity on the MRI image in a domain of the multi-scale transformation.

6. The apparatus according to claim 1, wherein the processing circuitry is further configured to determine the threshold using a calibration measurement representing a noise level of the MRI data.

7. The apparatus according to claim 1, wherein the processing circuitry is further configured to determine the threshold by setting the threshold to a value of a predetermined percentile of a histogram of the transformation coefficients of the one of the plurality of subbands.

8. The apparatus according to claim 7, wherein the processing circuitry is further configured to select a finest scale subband of the plurality of subbands as the at least one of the plurality of subbands.

9. The apparatus according to claim 1, wherein the processing circuitry is further configured to select a finest scale subband of the plurality of subbands as the at least one of the plurality of subbands.

10. The apparatus according to claim 1, wherein the processing circuitry configured to determine, based on at least one of the plurality of subbands, the threshold between signal and noise of the transformation coefficients comprises processing circuitry configured to determine (1) a first threshold between signal and noise of the transformation coefficients of a first group of the plurality of subbands and (2) a second threshold between signal and noise of the transformation coefficients of a second group of the plurality of subbands having a scale that is coarser than the first group, and
wherein the processing circuitry configured to reconstruct the MRI image comprises processing circuitry configured to reconstruct the MRI image from the MRI data using a regularized method in which a two-regularization-term objective function is minimized, the two-regularization-term objective function including a data fidelity term, a first regularization term that is scaled based on the first determined threshold, and a second regularization term that is scaled based on the second determined threshold.

11. The apparatus according to claim 1, wherein the threshold is common to plural subbands of the plurality of subbands.

12. A method comprising:
obtaining magnetic resonance imaging (MRI) data, the MRI data being acquired by non-uniformly sampling k-space;
performing a multi-scale transformation on a preliminary image generated from the MRI data and generating thereby a plurality of subbands, each of the plurality of subbands comprising respective transformation coefficients of the multi-scale transformation;
determining, based on at least one of the plurality of subbands, a threshold between signal and noise of the transformation coefficients; and
reconstructing an MRI image from the MRI data using a regularized method in which an objective function is minimized, the objective function including a data fidelity term and a regularization term that is scaled based on the determined threshold between the signal and the noise of the transformation coefficients.

13. The method according to claim 12, wherein determining the threshold is performed using one or more of a clustering-based thresholding method, an Otsu's method, a k-means clustering method, a mixture-model based method, and/or a method that includes setting the threshold to a value of a predetermined percentile of a histogram of the transformation coefficients of the one of the plurality of subbands.

14. The method according to claim 12, wherein performing the multi-scale transformation is performed using one of a wavelet transformation, a curvelet transformation, a Gaussian pyramid, a Laplacian pyramid, a steerable pyramid, a Gabor transformation, a blocked discrete cosine transformation or blocked discrete Fourier transformation, and/or a Haar transformation.

15. The method according to claim 12, wherein reconstructing the MRI image further includes that the objective function is minimized wherein the regularization term imposes sparsity on the MRI image in a domain of the multi-scale transformation.

16. A non-transitory computer readable storage medium including executable instructions, wherein the instructions, when executed by circuitry, cause the circuitry to perform the method according to claim 12.

* * * * *